(12) United States Patent
Soto-Álvarez et al.

(10) Patent No.: US 8,969,019 B2
(45) Date of Patent: Mar. 3, 2015

(54) DIAGNOSIS OF A PARASITIC DISEASE SUCH AS LEISHMANIASIS USING RIBOSOMAL PROTEIN EXTRACT (RPE)

(75) Inventors: Manuel Soto-Álvarez, Madrid (ES); Laura Ramírez-García, Madrid (ES); Eduardo Antonio Ferraz Coelho, Belo Horizonte (BR); Carlos Alonso-Bedate, Madrid (ES)

(73) Assignee: Laboratorios Leti, S.L., Madrid (ES)

( * ) Notice: Subject to any disclaimer, the term of this patent is extended or adjusted under 35 U.S.C. 154(b) by 0 days.

(21) Appl. No.: 13/383,482

(22) PCT Filed: Jul. 13, 2010

(86) PCT No.: PCT/EP2010/060058
§ 371 (c)(1),
(2), (4) Date: Mar. 26, 2012

(87) PCT Pub. No.: WO2011/006891
PCT Pub. Date: Jan. 20, 2011

(65) Prior Publication Data
US 2012/0178109 A1  Jul. 12, 2012

Related U.S. Application Data

(60) Provisional application No. 61/267,214, filed on Dec. 7, 2009.

(30) Foreign Application Priority Data

Jul. 13, 2009  (EP) ..................................... 09165282

(51) Int. Cl.
*G01N 33/569*  (2006.01)

(52) U.S. Cl.
CPC ...... *G01N 33/56905* (2013.01); *G01N 2469/20* (2013.01)
USPC ...................................................... 435/7.22

(58) Field of Classification Search
CPC .................... G01N 2469/20; G01N 33/56905
See application file for complete search history.

(56) References Cited

U.S. PATENT DOCUMENTS 6,500,437 B1  12/2002  Reed et al.
6,613,337 B1   9/2003  Reed et al.

FOREIGN PATENT DOCUMENTS

| EP | 1179733 A  | 2/2002 |
| EP | 1279679 A1 | 1/2003 |
| EP | 1624063 A  | 2/2006 |
| WO | WO 9633414 A | 10/1996 |

OTHER PUBLICATIONS

Soto et al. (J. Clin. Microbiol., 36:58-63, 1998).*
Iborra et al. (Microbes Infect., 10:1133-1141, 2008, available online Jun. 17, 2008.*
Skeiky, Y.A.W. et al., "Antigens Shared by *Leishmania* Species and *Trypanosoma cruzi*: Immunological Comparison of the Acidic Ribosomal PO Proteins", Infection and Immunity,62:1643-1651 (May 1994).
Skeiky, Y.A.W. et al., "Cloning and Expression of *Trypanosoma cruzi* Ribosomal Protein PO and Epitope Analysis of Anti-PO Autoantibodies in Chagas' Disease Patients", Journal of Experimental Medicine, 176:201-211 (Jul. 1992).
Barbosa-De-Deus, Rosangela, et al., "*Leishmania* Major-Like Antigen for Specific and Sensitive Serodiagnosis of Human and Canine Visceral Leishmaniasis," Clinical and Diagnostic Laboratory Immunology, vol. 9, No. 6, pp. 1361-1366 (Nov. 2002).
Cenini, Pietro, et al., "Ribosome-Inactivating Proteins from Plants Inhibit Ribosome Activity of *Trypanosoma* and *Leishmania*," J. Protozool, vol. 35, No. 3, pp. 384-387 (1998).
Cordeiro-Da-Silva, Anabela, et al., "Dual Role of the *Leishmania* Major Ribosomal Protein S3a Homologue in Regulation of T-and B-Cell Activation," Infection and Immunity, vol. 69, No. 11, pp. 6588-6596 (Nov. 2001).
Gonzalez, A. C., et al., "Molecular and Immunological Characterization of L14 Ribosomal Protein from *Leishmania braziliensis*," Parasitology, vol. 128, pp. 139-147 (2004).
Iborra, S., et al., "The Immunodominant T Helper 2 (Th2) Response Elicited in BALB/c Mice by the *Leishmania* LiP2a and LiP2b Acidic Ribosomal Proteins Cannot Be Reverted by Strong Th1 Inducers," Clinical and Experimental Immunology, vol. 150, pp. 375-385 (2007).
Maarouf, Mohammad, et al., "Ribosomes of *Leishmania* are a Target for the Aminoglycosides," Parasitol Res., vol. 81, pp. 421-425 (1995).
Preston, P. M., et al., "Immunogenicity of a Ribosomal Antigen of *Leishmania enriettii*," Transactions of the Royal Society of Tropical Medicine and Hygiene, vol. 65, No. 1, pp. 18-19 (1971).
Skeiky, Yasir A., et al., "A Recombinant *Leishmania* Antigen that Stimulates Human Peripheral Blood Mononuclear Cells to Express a Th1-Type Cytokine Profile and to Produce Interleukin 12," J. Exp. Med., vol. 181, pp. 1527-1537 (Apr. 1995).
Official action dated Apr. 14, 2014 from the Russian Federation Patent Office for RU 2012104855/10 and English translation.
Soto, M., et al., The *Leishmania infantum* Acidic Ribosomal Protein LiP2a Induces a Prominent Humoral Response in Vivo and Stimulates Cell Proliferation In Vitro and Interferon-Gamma (IFN-Gamma) Production by Murine Splenocytes, Clinical Exp. Immunol., vol. 122, No. 2, pp. 212-218 (2000)—Abstract.
Soto, M., et al., "Multicomponent Chimeric Antigen for Serodiagnosis of Canine Visceral Leishmaniasis," Journal of Clinical Microbiology, vol. 36, No. 1, pp. 58-63 (Jan. 1998).
Santarem, N., et al., "Antibodies Against a Leishmania Infantum Peroxiredoxin as a Possible Marker for Diagnosis of Visceral Leishmaniasis and for Monitoring the Efficacy of Treatment," Immunology Letters 101, pp. 18-23 (2005).

* cited by examiner

*Primary Examiner* — Brian J Gangle
(74) *Attorney, Agent, or Firm* — Morgan, Lewis & Bockius LLP

(57) ABSTRACT

The invention relates to a diagnosis method for Leishmaniasis using a RPE.

14 Claims, 3 Drawing Sheets

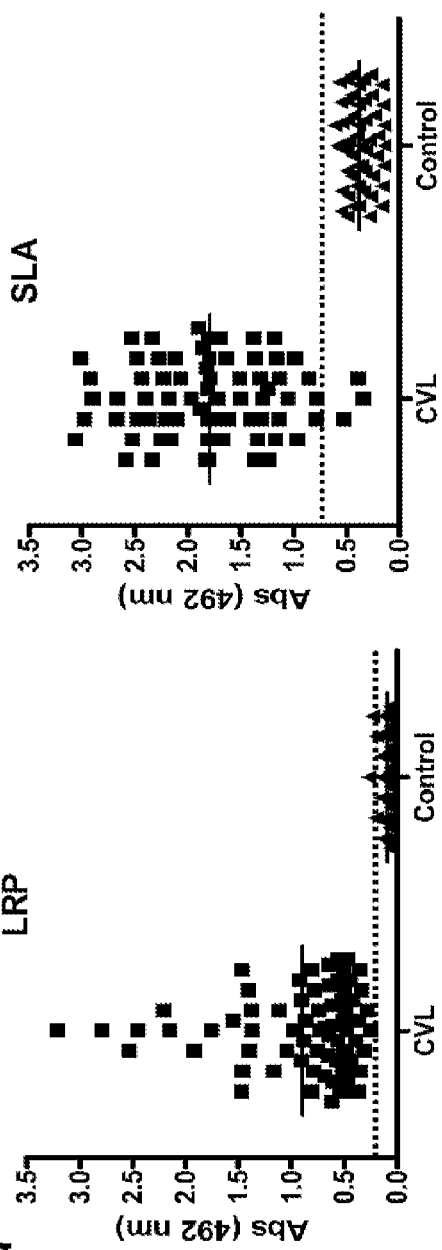
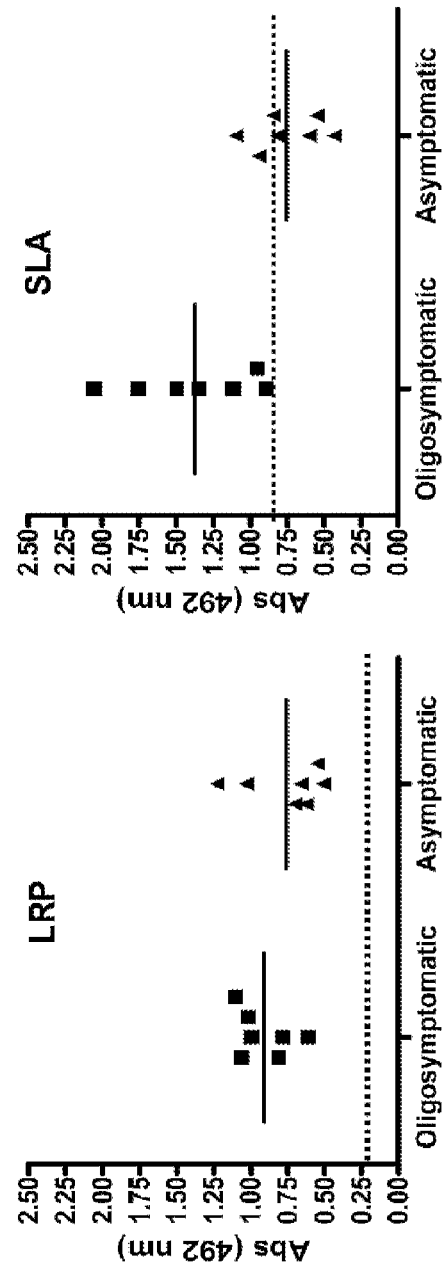
Fig 2a
Fig 2b

SEQUENCE LISTING

<160> NUMBER OF SEQ ID NOS: 1

<210> SEQ ID NO 1
<211> LENGTH: 322
<212> TYPE: PRT
<213> ORGANISM: Leishmaniasis chagasi

<400> SEQUENCE: 1

```
Met Pro Ser Ile Thr Thr Ala Lys Arg Glu Tyr Glu Arg Leu Val
1               5                   10                  15

Asp Cys Leu Thr Lys Tyr Ser Cys Val Leu Phe Val Gly Met Asp Asn
                20                  25                  30

Val Arg Ser Gln Gln Val His Asp Val Arg Arg Gly Cys Arg Gly Lys
            35                  40                  45

Ala Glu Phe Ile Met Gly Lys Lys Thr Leu Gln Ala Lys Ile Val Glu
    50                  55                  60

Lys Arg Ala Gln Ala Lys Asp Ala Ser Pro Glu Ala Lys Pro Phe Asn
65                  70                  75                  80

Asp Gln Cys Glu Glu Tyr Asn Leu Leu Ser Gly Asn Thr Gly Leu Ile
                85                  90                  95

Phe Thr Asn Asn Ala Val Gln Glu Ile Thr Ser Val Leu Asp Gly His
                100                 105                 110

Arg Val Lys Ala Pro Ala Arg Val Gly Ala Ile Pro Cys Asp Val Val
            115                 120                 125

Val Pro Ala Gly Ser Thr Gly Met Glu Pro Thr Gln Thr Ser Phe Phe
130                 135                 140

Gln Ala Leu Asn Ile Ala Thr Lys Ile Ala Lys Gly Met Val Glu Ile
145                 150                 155                 160

Val Thr Glu Lys Lys Val Leu Ser Val Gly Asp Lys Val Asp Asn Ser
                165                 170                 175

Thr Ala Thr Leu Leu Gln Lys Leu Asn Ile Ser Pro Phe Tyr Tyr Gln
                180                 185                 190

Val Asn Val Leu Ser Val Trp Asp Arg Gly Val Leu Phe Thr Arg Glu
            195                 200                 205

Asp Leu Met Met Thr Glu Asp Met Val Glu Lys Met Leu Met Glu Gly
    210                 215                 220

Leu Ser Asn Val Ala Ala Met Ala Leu Gly Ala Gly Ile Pro Thr Ser
225                 230                 235                 240

Ser Thr Ile Gly Pro Met Leu Val Asp Ala Phe Lys Asn Leu Leu Ala
                245                 250                 255

Val Ser Val Ala Thr Ser Tyr Glu Phe Glu Glu His Asn Gly Lys Glu
            260                 265                 270

Leu Arg Glu Ala Ala Ile Asn Gly Leu Leu Ala Gly Ser Gly Ser Ala
    275                 280                 285

Ala Ala Glu Pro Ala Ala Ala Pro Ala Ala Pro Ser Ala Ala Ala
        290                 295                 300

Lys Glu Glu Pro Glu Glu Ser Asp Glu Asp Phe Gly Met Gly Gly
305                 310                 315                 320

Leu Phe
```

DIAGNOSIS OF A PARASITIC DISEASE SUCH AS LEISHMANIASIS USING RIBOSOMAL PROTEIN EXTRACT (RPE)

FIELD OF THE INVENTION

The invention relates to a diagnosis method of a parasitic disease such as Leishmaniasis using a RPE.

BACKGROUND OF THE INVENTION

Canine visceral leishmaniasis (CVL) is an important emerging zoonosis in countries around the Mediterranean basin, in the Middle East, and in Latin America (20). This severe disease is caused by Leishmania infantum in the Mediterranean area, Middle-East and Asian countries and L. chagasi in Latin America (20, 21). Due to their genotypic relationships, both species causing CVL in different continent can be considered identical (26).

Upon infection dogs can develop different forms of the disease; asymptomatic, oligosymptomatic or symptomatic (4). Symptomatic infection results in death and its clinical manifestations include cutaneous alterations like alopecia, dermatitis, onychogryphosis (3, 11), and also visceral manifestations with renal, hepatic and cerebral alterations (18, 28). Some of the infected dogs remain asymptomatic or develop few mild symptoms and are classified as oligosymptomatic (4). CVL can not be considered only as a veterinary disease since infected dogs (even asymptomatic ones) are the main domestic reservoir of the parasite for human infection (1). Thus, to reduce the transmission of Leishmania from dogs to humans it is necessary to diagnose canine leishmaniasis as early as possible.

The presence of anti-Leishmania specific antibodies in asymptomatic, oligosymptomatic and symptomatic infected dogs (4, 9, 34) has allowed the development of serologic tests including immunofluorescent antibody test (IFAT), western blot, immunochromatographic test, and enzyme-linked immunosorbent assay (ELISA) (reviewed in (23)). Diagnosis of CVL using ELISA assays based on crude soluble Leishmania antigens (SLA) have shown to have high sensitivity but low specificity because of antigenic relatedness between Leishmania and other pathogenic protozoa (16). As a strategy to develop specific serodiagnostic test for CVL, different parasite antigens were obtained as recombinant proteins (5, 10, 24). However, due to the high variability observed in the humoral response of individual infected dogs against different parasite antigens (19, 31), efficient diagnosis based on recombinant proteins may require a mixture of recombinant proteins or the use of chimerical proteins containing several non-related parasite antigens (6, 31, 36). Specific diagnosis of CVL can be also developed using crude parasite fractions analyzed by western blotting or preparations purified from the parasite (8, 17). For example, an ELISA assay based on soluble Leishmania antigen (SLA) has already been developed (27, 31). However, this SLA-based assay is not enough specific for diagnosing asymptomatic Leishmaniasis. In addition, the sera from subjects having other parasite diseases distinct from Leishmaniasis will give false positive reaction with a SLA-based assay. Therefore, there is still a need for an improved diagnostic method of a parasitic disease such as Leishmaniasis, which does not have all the drawbacks of existing methods.

DESCRIPTION OF THE INVENTION

In this work, we show that a RPE, especially a Leishmania RPE (LRPE) could be advantageously used for diagnosing a parasitic disease such as Leishmaniasis: this new diagnosis method is more specific than known diagnosis methods such as a SLA-based method as demonstrated in the example. This new method allows a pre-symptomatic diagnosis of Leishmaniasis which is crucial in order to prevent or reduce the transmission of Leishmania from dogs to humans.

The invention is further described below.

Use

In a first aspect, there is provided a use of a Ribosomal Protein Extract (RPE) for diagnosing a parasitic disease in a subject.

As defined herein, a Ribosomal Protein Extract is obtainable by carrying out the following steps using a parasite cell causing a parasitic disease when present in a subject:
  a. mixing a parasite cell with a lysis buffer,
  b. centrifuging the obtained mixture to obtain a cytosolic extract,
  c. preparing the Ribosomal Protein Extract from the obtained cytosolic extract.

In step a, a parasite preferably means a protozoa. Preferred parasites are defined later herein. More preferably, a protozoa is in the promastigote stage. The skilled person will know the amount of parasite cells approximately needed in order to prepare a desired amount of RPE. Typically for preparing 500 micrograms of RPE, one will use $3.10^9$ parasite cells. A lysis buffer is a buffer, which will break down at least some of the parasite cells. At least part preferably means at least 50% of the cells, or at least 60%, 70%, 80%, 90% or 100%. A preferred lysis buffer comprises a non-ionic surfactant. Good results were obtained with NONIDET P 40 (NP40) as non-ionic surfactant.

Good results were obtained with Nonidet P 40 (NP40) as non-ionic surfactant. However, other non-ionic surfactant may be used. A preferred lysis buffer used is as follows (Buffer A): 10 mM Tris HCl, pH 8.0, 150 mM NaCl, 1.5 mM $MgCl_2$ and 0.5% NP40 (Roche) and preferably supplemented with protease inhibitors such as PMSF 1 mM, Leupeptin 8 μg/ml, Aprotinin 4 μg/ml and Pentatin 8 μg/ml). A suitable amount of parasite cells ($10^9$ cells/ml buffer A) is typically gently mixed with this lysis buffer using an eppendorf pipet.

In step b, at least one step of centrifugation at 4° C. is applied on the obtained mixture of step a. Usually a first centrifugation step is carried out at 3,000 g for 2 minutes. The obtained supernatant is preferably again centrifuged at 13,000 g for 15 minutes at 4° C. once or twice.

In step c, the obtained supernatant is used for preparing a RPE. Briefly, the obtained supernatant is submitted to high speed centrifugation at 90,000 rpm for 30 min at 4° C. A rotor used is preferably a Beckman TL 100.3 rotor. The obtained pellet is a crude ribosomal pellet, which is resuspended in a suitable buffer such as buffer B (20 mM Tris-HCl, pH 7.4, 500 mM $AcNH_4$, 100 mM $MMgCL_2$, 5 mM β-mercaptoethanol) and centrifuged through a discontinuous sucrose gradient (20/40%) in a suitable buffer such as buffer A at 90,000 rpm at 4° C. Here again, a preferred rotor is a TL 100.3 rotor. The obtained pellet comprises ribosomes. This pellet is preferably dissolved in PBS (Phosphate Buffer Saline), sonicated and stored at −70° C.

Ribosomal proteins are well conserved cytosolic proteins. Therefore, a RPE as defined herein, may be prepared from any eukaryotic organism, be it plant or animal, be it from mammals, reptiles, fish, insects, or any other chromosome bearing organism, such as protozoa. Preferably a RPE is obtained from an organism which is close to the disease, preferably parasitic disease causing organism in the evolutionary tree. Therefore, of particular interest as a source of RPE to be used in the treatment of a parasitic disease are protozoans like plasmodium and in particular members of the trypanosomatid family, more in particular different species of the trypanosomatical protozoan *Leishmania* or *Trypanosoma*. There are over 20 known species of *Leishmania*, including species of the subgenus *Leishmania*, comprising the complex *L. major*, including *L. major*, the complex *L. Donovani*, including *L. chagasi*, *L. donovani* and *L. infantum*, the complex *L. Mexicana*, including *L. amazonensis* and *L. mexicana*, as well as the subspecies *Viannia*, comprising the complex *L. braziliensis*, including *L. braziliensis* and *L. peruviana* and the complex *L. guyanensis*, including *L. guyanensis* and *L. panamensis*. *Plasmodium* species of particular interest are *Plasmodium falciparum* and *Plasmodium vivax*. In a preferred embodiment, a RPE is obtained from a *Leishmania* species, preferably *Leishmania major* and/or *Leishmania infantum*. In another preferred embodiment, a RPE is obtained from a *Plasmodium* species. The skilled person will understand that a RPE may also be prepared by mixing a RPE from several distinct organims as identified herein. The use of a RPE in a diagnostic method of the invention instead of the use of a given protein is quite attractive since a RPE contains a large number of distinct antigens. Each of these antigens could potentially diagnose the presence of an immune response in a subject. Moreover, there are subjects that respond to antigen A and not to B and vice versa. Therefore, a RPE as used herein is intended to be used for a broad population of subjects since it contains a large number of distinct antigens. In a preferred embodiment, a RPE comprises at least one ribosomal protein and/or at least one antigen of a ribosomal protein and/or at least one protein fragment of a ribosomal protein. In a more preferred embodiment, a RPE comprises at least two ribosomal proteins and/or at least two antigens of a ribosomal protein and/or at least two protein fragments of a ribosomal protein. A protein fragment as defined herein is preferably a fragment comprising at least 2, 3, 5, 7, 10, 15, 20, 25, 30 or more contiguous amino acids of a corresponding ribosomal protein. In an embodiment, a RPE as defined herein does not comprise or does not consist of the acidic ribosomal protein P0 of *Leishmania infantum* and/or the ribosomal antigen LbeF4A from *Leishmania braziliensis*. In another embodiment, a RPE as defined herein does not comprise or does not consist of an epitope originating from the acidic ribosomal antigen LcPo from Leishmaniasis chagasi as disclosed in EP 824 699. More preferably, a RPE does not comprise or consist of the 17 amino acids situated at the C-terminal of LcPo: amino acids 306-322 of LcPo represented by SEQ ID NO:2 in EP 824 699, which is also identified as SEQ ID NO:1 in the sequence listing.

One advantage of the present invention is that it allows to reach a specific and early diagnostic of a broader spectrum of parasitic diseases. One example of a parasitic disease in which this is the case is Leishmaniasis. In a preferred embodiment, a parasitic disease is Leishmaniasis or *malaria*. More preferably, a parasitic disease is caused by a *Leishmania* or by a *Plasmodium* species. In a further preferred embodiment, a parasitic disease is caused by a different species than the species from which a RPE is derived. In particular, Leishmaniasis caused by one species from the genus *Leishmania* may be diagnosed by using a composition based on a RPE from another *Leishmania* species. In one embodiment, Leishmaniasis caused by *L. major* is successfully diagnosed with a composition comprising a RPE from *L. infantum*. Alternatively, other parasitic diseases, such as *malaria*, may be successfully diagnosed with a composition based on a RPE of another species, for instance based on a RPE of *L. infantum*.

In the context of the invention, a subject means a human or an animal. An animal which is encompassed within the scope of the invention includes a mammal, preferably a human or a dog. In principle, any subject could be diagnosed using the invention. The diagnosis method may be applied as often as necessary in a subject. Preferably, a subject diagnosed is a subject suspected to have a risk of having been infected with said parasite causing said parasitic disease. A subject suspected to have a risk of having been infected with said parasite may live in an endemic area or has been visiting an endemic area. An endemic area includes North Africa from Algeria to Saudi Arabia, Kenya, Sudan, Ethiopia. It further includes Southern Europe: Mediterranean countries Spain, France, Greece, etc. It also includes Central (All countries) and South America: Brazil, Venezuela, Peru, Bolivia, Colombia North of Argentina, Paraguay, Uruguay, Central to South West Asia: India, Iran, Iraq, Mongolia, Nepal, Bangladesh.

In the context of the invention, a use as defined herein is preferably an in vitro or ex vivo use. It preferably means that said use is carried out on a sample from said subject. Preferred samples include blood, serum, plasma, saliva, cerebrospinal fluid or urine. More preferably, the sample is a blood or serum sample obtained from a subject.

In a preferred embodiment, a diagnosis is reached before the apparition of a symptom of said parasitic disease, so-called pre-symptomatic diagnosis or diagnosis of an asymptomatic subject. In this context, "pre-symptomatic" preferably means at least one day, at least two days, at least three days, at least four days, at least five days, at least six days, at least seven days, at least eight days, at least nine days, at least ten days at least 15 days, at least 20 days, at least 25 days, at least 30 days or more before the apparition of a first symptom. A first symptom or a first clinical sign associated with a parasitic disease such as Leishmaniasis may be selected from the following list: fever, splenomegaly, hepatomegaly, lymphadenopathy, conjunctivitis, dermatitis onychogriphosis, keratoconjunctivitis, apathy and cachexia. Most of them can be simple detected by physical external examination. Each of conjunctivitis, dermatitis, onychogriphosis, keratoconjunctivitis is a form of cutaneous alteration.

A preferred first symptom linked to Leishmaniasis is lymphadenopathy. It can be detected by physical external examination such as palpation.

In another preferred embodiment, a diagnosis is reached before the apparition of some of the symptoms of said parasitic disease, so-called diagnosis of an oligosymptomatic subject. In this context, "oligosymptomatic" preferably means a subject having a maximum of three of the symptoms as defined above.

In another preferred embodiment, a diagnosis is reached before the apparition of all symptoms of said parasitic disease, so-called diagnosis of an symptomatic subject. In this context, "symptomatic" preferably means a subject having at least four of the symptoms as defined above including a form of cutaneous alteration as defined above.

The skilled person will understand that the most important type of diagnosis is the diagnosis of asymptomatic subjects, since it will help preventing the further spreading of the disease and asymptomatic subjects could be helped and cured more efficiently if they are diagnosed in such a stage.

Method

In a second aspect there is provided an method for diagnosing a parasitic disease in a subject using RPE, the method comprising determining whether an antibody recognizing RPE is present in a sample obtained from the subject. A preferred method of the invention is as for a preferred use of the invention preferably carried out in vitro or ex vivo. A definition has been given earlier herein.

In a preferred method, RPE is present in a composition. RPE has been been defined earlier herein. In a preferred embodiment, another compound is present is said composition. Alternatively, no other compound is present in said composition.

In a preferred embodiment, other compounds are used sequentially or simultaneously with RPE in order to improve the specificity of the method. It is advantageous for example to use other compounds that will be able to discriminate between asymptomatic, oligosymptomatic or symptomatic subject and vaccinated subject. More preferably, such compounds are not present in a single composition together with RPE. For example other non-related antigen of a parasite causing said parasitic disease (31) such as Leishmaniasis may be used. Another example is the use of poly-proteins containing several parasite antigens (6, 36). Preferred antigens include a histone protein or fragment thereof or a nucleic acid molecule encoding said histone. More preferably, a histone protein is H2A, H2B, H3 and/or H4 as identified in EP 1 687 023. Histones H2A, H2B, H3 and H4 are well-conserved nuclear proteins and their sequence is well-known in the art, see e.g. Requena et al., Trends in Parasitol. (2000) 16:246. Preferably the histones are obtained from an organism which is close to the disease causing organism in the evolutionary tree. Therefore, of particular interest as a source of histones to be used in the treatment of parasitic diseases such as Leishmaniasis are protozoans and in particular members of the trypanosomatid family, as for example plasmodium, more in particular different species of the trypanosomatical protozoan *Leishmania*.

In a more preferred diagnosis method, a parasitic disease is diagnosed when a detectable amount of an antibody recognizing RPE is present and/or when an increase of the amount of said antibody is present. In a control or healthy subject, said antibody is generally not detectable.

Detection of the presence of said antibody is carried out using methods known to the skilled person such as an ELISA. Preferred ways of detection are described in the section entitled assay.

An antibody recognizing RPE preferably means that at least one antibody is present which is able to recognize at least one compound present in RPE. Said compound may be a ribosomal protein or a ribosomal protein fragment or a ribosomal antigen of a ribosomal protein.

Assay

In a third aspect, there is provided an assay device or an assay for diagnosing a parasitic disease in a subject, wherein the device or the assay comprises RPE. The presence of an antibody specifically recognizing RPE may be detected by any standard methods known to those skilled in the art (see, e.g., Harlow and Lane, Antibodies: A Laboratory Manual, Cold Spring Harbor Laboratory, 1988, which is incorporated herein by reference). Suitable methods include affinity chromatography co-electrophoresis (ACE) assays and (Enzyme-Linked Immuno Sorbent Assay) ELISA. Preferably, the assay comprises an ELISA. Several assays are more extensively described below.

In a preferred embodiment, an assay involves the use of RPE immobilized on a solid support to bind to and remove an antibody from the sample. Said bound antibody may then be detected using a detection reagent that binds to the antibody/RPE complex and contains a detectable reporter group. Suitable detection reagents include antibodies that bind to the antibody/RPE complex and free polypeptide labeled with a reporter group (e.g., in a semi-competitive assay). Alternatively, a competitive assay may be utilized, in which an antibody that binds to RPE is labelled with a reporter group and allowed to bind to the immobilized RPE after incubation of the RPE with the sample. The extent to which components of the sample inhibit the binding of the labelled antibody to RPE is indicative of the reactivity of the sample with the immobilized RPE.

A solid support may be any material known to those of ordinary skill in the art to which RPE may be attached. For example, a support may be a test well in a microtiter plate or a nitrocellulose or other suitable membrane. Alternatively, a support may be a bead or disc, such as glass, fiberglass, latex or a plastic material such as polystyrene or polyvinylchloride. A support may also be a magnetic particle or a fiber optic sensor, such as those disclosed, for example, in U.S. Pat. No. 5,359,681.

RPE may be bound to the solid support using a variety of techniques known to those in the art. In the context of the present invention, the term "bound" refers to both non-covalent association, such as adsorption, and covalent attachment (which may be a direct linkage between the antigen and functional groups on the support or may be a linkage by way of a cross-linking agent). Binding by adsorption to a well in a microtiter plate or to a membrane is preferred. In such cases, adsorption may be achieved by contacting RPE, in a suitable buffer, with the solid support for a suitable amount of time. The contact time varies with temperature, but is typically between 1 hour and 1 day. In general, contacting a well of a plastic microtiter plate (such as polystyrene or polyvinylchloride) with an amount of RPE ranging from 10 ng to 1 g, and preferably 100 ng, is sufficient to bind an adequate amount of RPE.

Covalent attachment of RPE to a solid support may generally be achieved by first reacting the support with a bifunctional reagent that will react with both the support and a functional group, such as a hydroxyl or amino group, on the polypeptide. For example, RPE may be bound to a support having an appropriate polymer coating using benzoquinone or by condensation of an aldehyde group on the support with an amine and an active hydrogen on the polypeptide (see, e.g., Pierce Immunotechnology Catalog and Handbook (1991) at A12-A13).

In certain embodiments, an assay is an enzyme linked immunosorbent assay (ELISA). This assay may be performed by first contacting a RPE that has been immobilized on a solid support, commonly the well of a microtiter plate, with the sample, such that antibodies specific for RPE within the sample are allowed to bind to the immobilized RPE. Unbound sample is then removed from the immobilized RPE and a detection reagent capable of binding to the immobilized antibody-RPE complex is added. The amount of detection reagent that remains bound to the solid support is then determined using a method appropriate for the specific detection reagent.

Once the RPE is immobilized on the support, the remaining protein binding sites on the support are typically blocked. Any suitable blocking agent known to those of ordinary skill in the art, such as bovine serum albumin (BSA) or TWEEN 20 (Sigma Chemical Co., St. Louis, Mo.) may be employed. The immobilized RPE is then incubated with the sample, and antibody (if present in the sample) is allowed to bind to the RPE. A sample may be diluted with a suitable diluent, such as phosphate-buffered saline (PBS) prior to incubation. In general, an appropriate contact time (i.e., incubation time) is that period of time that is sufficient to permit detect the presence of antibody within a sample. Preferably, the contact time is sufficient to achieve a level of binding that is at least 95% of that achieved at equilibrium between bound and unbound antibody. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% TWEEN 20. Detection reagent may then be added to a solid support. An appropriate detection reagent is any compound that binds to the immobilized antibody-RPE complex and that can be detected by any of a variety of means known to those in the art. Preferably, the detection reagent contains a binding agent (such as, for example, Protein A, Protein G, immunoglobulin, lectin or free antigen) conjugated to a reporter group. Preferred reporter groups include enzymes (such as horseradish peroxidase), substrates, cofactors, inhibitors, dyes, radionucleides, luminescent groups, fluorescent groups and biotin. The conjugation of binding agent to reporter group may be achieved using standard methods known to those of ordinary skill in the art. Common binding agents may also be purchased conjugated to a variety of reporter groups from many sources (e.g., Zymed Laboratories, San Francisco, Calif. and Pierce, Rockford, Ill.).

The detection reagent is then incubated with the immobilized antibody RPE complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the reporter group.

The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of an antibody specific for a parasitic disease such as Leishmaniasis in a sample, the signal detected from the reporter group that remains bound to the solid support is generally compared to a signal that corresponds to a predetermined cut-off value. In one preferred embodiment, the cut-off value is preferably the average mean signal obtained when the immobilized RPE is incubated with a sample from an uninfected subject. In general, a sample generating a signal that is three standard deviations above the predetermined cut-off value is considered positive (i.e., reactive with RPE). In an alternate preferred embodiment, the cut-off value is determined using a Receiver Operator Curve, according to the method of Sackett et al., Clinical Epidemiology: A Basic Science for Clinical Medicine, p. 106-7 (Little Brown and Co., 1985). Briefly, in this embodiment, the cut-off value may be determined from a plot of pairs of true positive rates (i.e., sensitivity) and false positive rates (100%-specificity) that correspond to each possible cut-off value for the diagnostic test result.

The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate.

In a related embodiment, an assay is performed in a flow-through or strip test format, wherein RPE is immobilized on a membrane such as nitrocellulose. In the flow-through test, antibodies within the sample bind to the immobilized RPE as the sample passes through the membrane. A detection reagent (e.g., protein A-colloidal gold) then binds to the antibody-RPE complex as the solution containing the detection reagent flows through the membrane. The detection of bound detection reagent may then be performed as described above. In the strip test format, one end of the membrane to which RPE is bound is immersed in a solution containing the sample. The sample migrates along the membrane through a region containing detection reagent and to the area of immobilized polypeptide. Concentration of detection reagent at RPE indicates the presence of an antibody specific for an antigen of a parasite causing a parasitic disease such as Leishmaniasis in the sample. Typically, the concentration of detection reagent at that site generates a pattern, such as a line, that can be read visually. The absence of such a pattern indicates a negative result. In general, the amount of RPE immobilized on a membrane is selected to generate a visually discernible pattern when a sample contains a level of antibody that would be sufficient to generate a positive signal in an ELISA, as discussed above. Preferably, the amount of RPE immobilized on a membrane ranges from 25 ng to 500 ng. Such tests can typically be performed with a very small amount (e.g., one drop) of subject serum or blood.

Any subject or physician could use this device at office/home, repeat the use of such device or assay as often as necessary.

Usually additional molecules are used in an assay as a positive or negative control. A typical positive control could be an antibody recognizing a molecule which is known to be present in a sample to be tested. A typical negative control could be an antibody recognizing a molecule which is known to be absent in a sample to be tested.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a product, an assay device respectively a method or a use as defined herein may comprise additional component(s) respectively additional step(s) than the ones specifically identified, said additional component(s), respectively step(s) not altering the unique characteristic of the invention.

In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The invention is further illustrated by the following example, which should not be construed for limiting the scope of the present invention.

DESCRIPTION OF THE FIGURES

FIG. 2. Comparative evaluation of the diagnostic sensitivity of LRP and SLA. (A) ELISA reactivity of sera from dogs with symptomatic CVL and control sera with LRP and SLA. (B) ELISA reactivity of sera from dogs with oligosymptomatic and asymptomatic CVL with LRP and SLA. The mean value of the CVL sera is shown. Broken bars show the cut-off value defined as the mean optical density plus three standard deviations of the values obtained with sera from healthy controls.

EXAMPLES

Materials and Methods

Figure 1A:
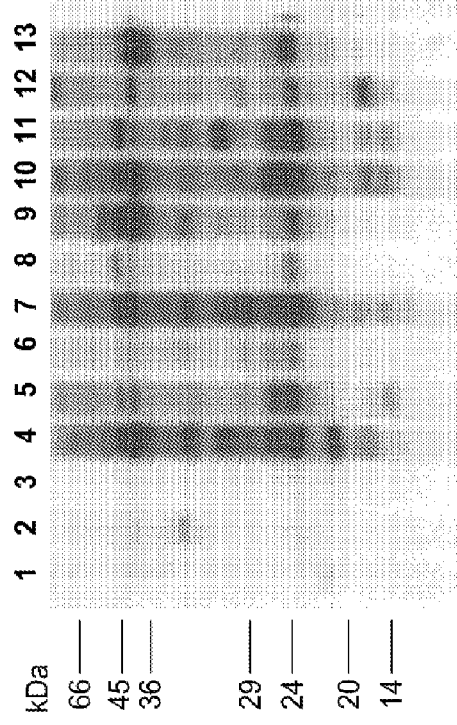
FIG. 1. (A) *L. infantum* ribosomal proteins were electrophoresed on a linear 10-14% gradient SDS-PAGE gel, transferred onto a nitrocellulose membrane and incubated with the sera of healthy dogs (lanes 1-3), and sera from dogs naturally infected with *L. infantum* having symptomatic CVL (lanes 4-13). Individual sera were employed at a 1:200 dilution. (B) 2D-PAGE of *L. infantum* ribosomal proteins. Left panel shows a representative silver stained gel. A similar gel was transferred onto a nitrocellulose membrane and incubated with a pool of the CVL sera (1:200) used in (A). A horseadish peroxidase conjugated anti-dog IgG antibody was used as secondary reagent.

Parasites. *Leishmania chagasi* (MOM/BR/1970/BH46) and *L. infantum* (MCAN/ES/1996/BCN/150, MON-1) were grown at 24° C. in Schneider's (Sigma, St. Louis, Mo., USA) medium supplemented with 20% heat-inactivated fetal bovine serum (Sigma, St. Louis, Mo., USA), 20 mM L-glutamine, 200 U/mL of penicillin, 100 µg/mL of streptomycin and 50 µg/mL of gentamicin at pH 7.4.

Antigen preparation. SLA was prepared from stationary phase promastigotes of *L. chagasi* and *L. infantum* after few passages in liquid culture, as previously described (12). Briefly, $2 \times 10^8$ promastigotes per mL, in a volume of 5 mL, were washed 3 times in cold sterile phosphate-buffered saline (PBS). After six cycles of freezing and thawing followed by ultrasonication (Ultrasonic processor, GEX600), with five cycles of 30 sec at 38 MHz, the suspension was centrifuged at 8.000 g for 30 min at 4° C. and supernatant containing SLA was collected. The protein concentration was estimated by the Bradford method (7) and aliquots of 500 µL were stored at −70° C.

LRP was prepared from logarithmic phase promastigotes of *L. infantum* as previously described (22). Briefly, $1 \times 10^9$ promastigotes were harvested, washed twice in pre-chilled PBS, resuspended in 1 ml NP40 lysis buffer (10 mM Tris HCl, pH 8.0, 150 mM NaCl, 1.5 mM $MgCl_2$ and 0.5% NP40) and pipetted up and down 10 times. After lyses, samples were microfuged at 3,000×g for 2 min at 4° C. to pellet the nuclei. Supernatant was twice microfuged at 13,000×g for 15 min at 4° C. The purified cytosolic supernatant was submitted to high speed centrifugation at 90,000 rpm for 30 min at 4° C. in a Beckman TL100.3 rotor. The crude ribosomal pellet was resuspended in buffer A (20 mM Tris-HCl, pH 7.4, 500 mM $AcNH_4$, 100 mM $MgCl_2$, 5 mM β-mercaptoethanol) and centrifuged through a discontinuous sucrose gradient (20/40%) in buffer A at 90,000 rpm at 4° C. in a TL100.3 rotor.

Serum samples. Serum samples were collected in Spain and Brazil. CVL serum samples from Spain were collected from 28 clinically symptomatic dogs in the Extremadura region. *L. infantum*-infected animals were clinically and analytically evaluated at the Department of Parasitology of the Veterinary School, Extremadura University, Cáceres, Spain. Animals were considered symptomatic when three or more of the following symptoms were present: loss of weight, alopecia, adenopathy, onychogryposis, hepatomegaly, conjunctivitis and exfoliative dermatitis on the nose, tail and ear tips. All sera were positive when tested by indirect immunofluorescence, and the presence of amastigote forms of the parasite was confirmed by direct observation in popliteal and prescapular lymphoid nodes. Control sera were obtained from 8 healthy animals (Department of Parasitology, Extremadura University).

Serum samples from 58 *L. chagasi*-infected dogs (44 clinically symptomatic, 7 oligosymptomatic and 7 asymptomatic) from Belo Horizonte area, Minas Gerais, Brazil, were used. As described above, animals were considered symptomatic when they present three or more of the clinical symptoms, oligosymptomatic when only one or two symptoms were present and asymptomatic when dogs were free from clinical symptoms. As above, diagnosis of VL was defined when amastigotes were seen in Giemsa stained smears of bone marrow aspirates or promastigotes were identified on culture of peripheral blood or bone marrow aspirates. Sera from brazilian dogs were provided by Evaldo Nascimento and Maria Norma Melo (Department of Parasitology, Universidade Federal de Minas Gerais, Belo Horizonte, Minas Gerais, Brazil). Serum from 47 dogs living in endemic areas from VL but with no clinical signs or suspicion of canine *leishmaniasis* and negative after parasitological and serological tests constituted to the control group. Fourteen serum samples from dogs with other parasite infections were used to analyze cross-reaction, as follows: *Toxoplasma gondii* (n=5) and *Trypanosoma cruzi* (n=9). Serum samples from healthy dogs and vaccinated with Leishmune® (n=18) or Leishtec® (n=23) vaccines, were used in the experiments.

ELISA. Microtiter immunoassay plates (Falcon) were coated with *L. infantum* or *L. chagasi* SLA, or with *L. infantum* LRP (0.5 µg/well, each one), in 100 µL of coating buffer pH 9.6, 18 h at 4° C. A titration curve was performed to determine the best protein concentration and antibody dilution to be used. Free binding sites were blocked with a PBS-TWEEN 20 0.05% (PBST) and 3% casein solution for 2 h at 37° C. After three washes with PBST, plates were incubated with 100 µL of canine sera for 1 h at 37° C. Serum samples were diluted 1:200 in PBST and 0.3% casein. Plates were washed seven times and incubated with 1:10.000 anti-dog IgG antibody (Sigma, St. Louis, USA) horseradish peroxidase conjugated. The reaction was developed by incubation with $H_2O_2$, orto-phenylenediamine and citrate-phosphate buffer pH 5.0, for 30 min in the dark and stopped by addition of 20 µL $H_2O_2$ 2 N. Optical densities were read at 492 nm in an ELISA microplate spectrophotometer (Molecular Devices, Spectra Max Plus. Concord, ON, Canada).

Western blot. For SDS-PAGE *L. infantum* LRPs (15 µg) were resuspended in Laemmli's buffer and resolved in 10-14% gradient SDS-PAGE gels with a preparative comb using the BioRad Protein electrophoresis minigel system (Hercules, CA, USA). For 2D-PAGE, *L. infantum* LRPs were solved in 200 µl of lysis buffer (0.5% NONIDET 40, 1 mM EDTA, pH 8.0, 0.1 mM PMSF, 10 mM Tris HCl, pH 7.4, and 1 mM DTT) and extracted with an equal volume of phenol. Proteins present in the organic phase were precipitated with five volumes of ammonium acetate buffer (0.1 M ammonium acetate dissolved in methanol) and washed three times with 80% acetone. The dry pellet was resuspended in rehydration buffer (7 M urea, 2M thiourea, 0.5% IPG buffer (3-10), 4% CHAPS, 40 mM Tris HCl, pH 8.8, and 0.002% bromophenol blue) and centrifuged to remove insoluble material. Proteins were adsorbed onto an IMMOBILINE™DryStrip, pH3-10, 11 cm (GE Healthcare, Uppsala, Sweden). Rehydration and isoelectric focusing (IEF) were performed using the IPGphor system (GE Healthcare) according to the manufacturer's instructions. After IEF, the IPG strips were equilibrated in equilibration buffer (6 M urea, 2% SDS, 0.375 M Tris HCl, pH 8.8, 20% glycerol, 0.002% bromophenol blue) plus 20 mg/ml DTT for 15 min, and then with equilibration buffer plus 25 mg/ml of iodoacetamide for another 15 min. Equilibrated IPG strips were placed onto 12% SDS-PAGE minigels (BioRad). The 2D-PAGE gel was stained with silver nitrate using the silver staining kit (GE Healthcare).

In both cases, and after electrophoresis, gels were transferred to nitrocellulose membranes (GE Healthcare). The blots were probed with the sera (1:200) from dogs infected with *L. infantum* individually (SDS-PAGE) or as a pool (2D-PAGE). As secondary antibody, horseradish peroxidase-conjugated anti-dog-IgG (1:2,000) purchased from Nordic Immunological Laboratories (Tilburg, The Netherlands) was used.

Statistical analysis. All data comparisons were tested for significance by using unpaired Student's t-test; P values <0.05 were considered statistically significant.

Results

Antigenicity of the *L. infantum* LRP during canine infection. In order to analyze the antigenicity of the LRP during canine infection, the sera from 10 dogs naturally infected with *L. infantum* were incubated with a nitrocellulose membrane containing the LRP extracts from this parasite. The sera of all the infected animals recognized this parasite purified protein fraction (FIG. 1A, lanes 4-13). The sera from healthy dogs were negative or faintly stained some polypeptides in the crude ribosomal preparation (FIG. 1A, lanes 1-3). Most of the CVL sera recognized a high number of protein bands although the recognition pattern complexity and intensity was different between individual dog sera. In spite of the variability observed two immunodominant regions were observed in the western blot: 45-36 kDa and 25-22 kDa polypeptides, respectively.

Figure 1B:
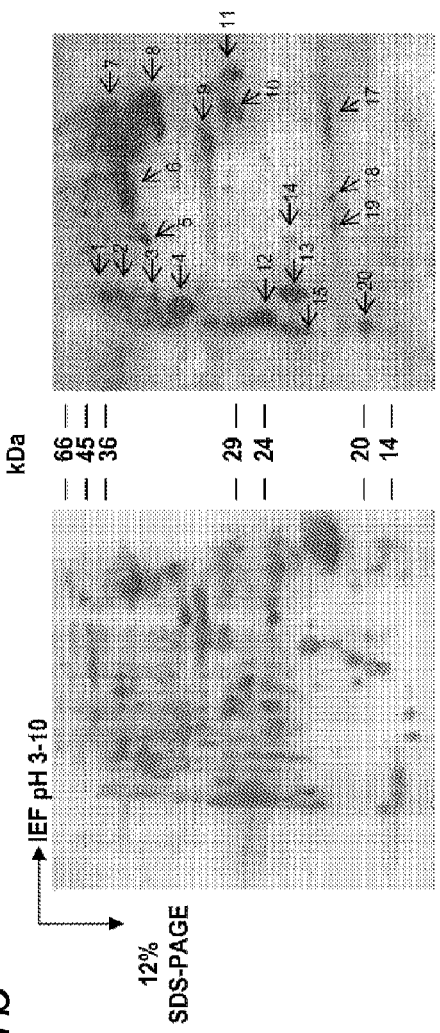

In order to analyze in higher detail the pattern of proteins recognized, the LRP extract was separated by high-resolution 2D-PAGE. As shown in FIG. 1B, right panel the gels prepared with preparative protein loadings (20 μg) displayed good resolution with only minimal streaking for the most basic proteins (FIG. 1, left panel). The presence of 20 antigenic spots was detected when a 2D-PAGE gel was incubated with a pool of the same sera employed above (FIG. 1B, right panel).

Comparison of LRP and SLA for the serodiagnosis of CVL. In order to determine whether the LRP extract could be considered a valuable tool for serodiagnosis of CVL, we analyzed the reactivity against LRP and SLA of 127 canine serum samples. The first sera group was composed by 72 serum samples obtained from *L. infantum* (n=28) or *L. chagasi* (n=44) infected symptomatic dogs. The second group was formed by the sera from 55 healthy dogs. FIG. 2A shows the absorbance values from symptomatic CVL and controls sera. For both protein preparations, differences between CVL and control sera were statistically significant (P<0.001). The spectrum of the absorbance values from LRP and SLA were different, being the reactivity of CVL sera against SLA higher (mean=1.79±0.64) than that obtained for LRP (mean=0.90±0.63). As indicated by the standard deviation (SD), high variability in the absorbance value from individual serum samples was observed for both antigenic preparations, although the SD was higher when SLA was employed as antigen. The reactivity of the healthy sera was also higher against SLA (mean=0.38±0.13) than against LRP (mean=0.0954±0.047). In the ELISA conditions indicated under Materials and Methods the cut-off value for both antigens (defined as the mean reactivity value from healthy sera plus 3 SD) was 0.237 for LRP and 0.774 for SLA. These cut-off values allowed us to identify positive and negative sera and consequently to estimate the performance parameters of the ELISA (Table 1). Since LRP showed similar performance (high sensitivity and specificity values) than SLA in ELISA assays it can be conclude that *Leishmania* ribosomal proteins are suitable antigens for the diagnosis of symptomatic CVL.

Next, the sera from oligosymptomatic (n=7) and asymptomatic (n=7) dogs were tested (FIG. 2B). The reactivity against LRP and SLA from the sera of both groups and the healthy control were found to be statistically significant (P<0.001). Although a limited number of sera were employed, the data obtained indicate that whereas the sera from oligosymptomatic dogs recognized the LRP and SLA preparations (100% sensitivity), the sera from 30% of the asymptomatic dogs (3/7) showed absorbance values against SLA higher than the cut-off value (FIG. 2B). On the other hand, the sera from all the asymptomatic dogs tested showed absorbance values against LRP higher than the cut-off value. Thus, our results indicate that the use of LRP can be considered as a good tool for serodiagnosis of CVL.

Figure 3A:
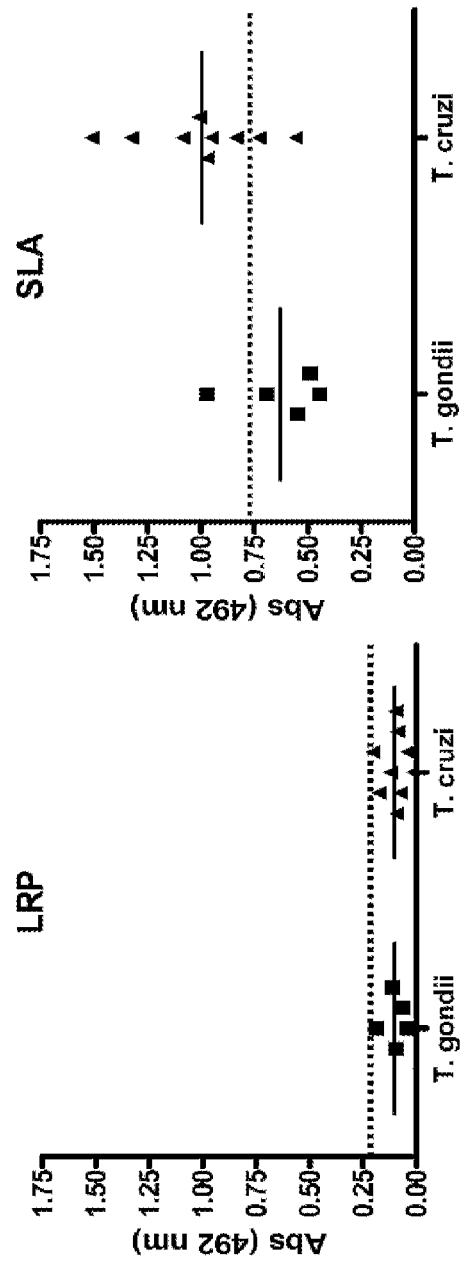
FIG. 3. Comparative evaluation of the diagnostic specificity of LRP and SLA. (A) ELISA reactivity of sera from dogs with infected with *T. gondii* or *T. cruzi* with LRP and SLA. (B) ELISA reactivity of sera from dogs vaccinated with Leishmune® or Leishtec® with LRP and SLA. The mean value of the CVL sera is shown. Broken bars show the cut-off value defined as the mean optical density plus three standard deviations of the values obtained with sera from healthy controls.

Cross-reactivity of LRP and SLA. Since LRP is composed of evolutive conserved proteins, we have analyzed the potential cross-reactions of the LRP extracts with the sera from dogs infected with other unicellular protozoa: *Toxoplasma gondii* (n=5) and *Trypanosoma cruzi* (n=9). In the FIG. 3, the reactivity values of the individual sera for each group against LRP are shown. None of the sera from *T. gondii* (mean=0.1012±0,056) or *T. cruzi* (mean=0.101±0.06) infected dogs showed a reactivity over the cut-off defined by the healthy sera (see above). As control, the reactivity of the same sera was assayed against SLA. The mean reactivity of these sera against SLA (0.629±0.21 for *T. gondii* and 0.99±0.29 for *T. cruzi* infected dogs) was higher than that observed against LRP. The reactivity of some of them was higher than the cut-off value (1/5 for *T. gondii* and 7/9 for *T. cruzi* infected dogs).

Figure 3B:
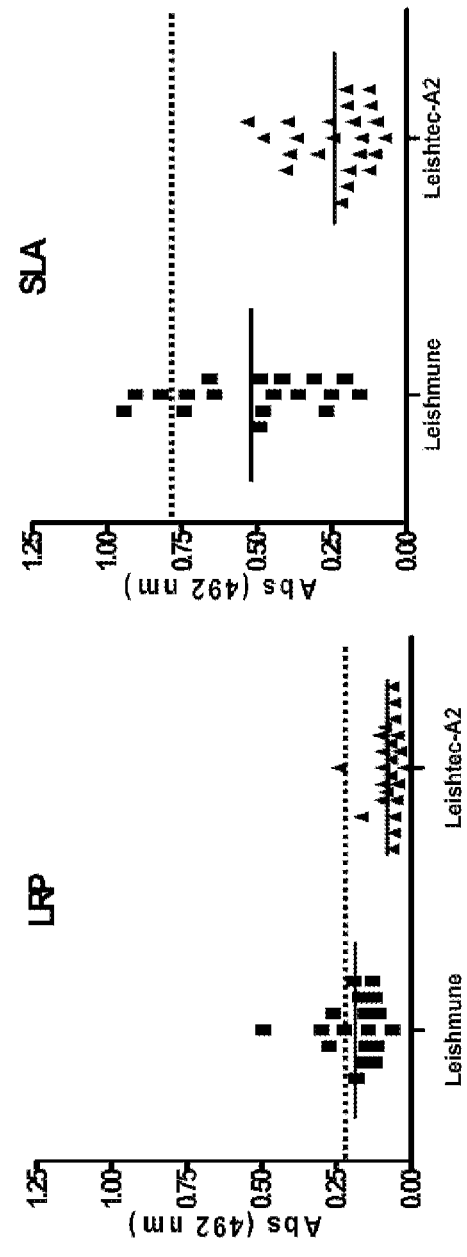

The reactivity of the sera from dogs vaccinated with two *Leishmania* prophylactic vaccines licensed in Brazil: Leishmune® (29) and Leishtec® (15).against LRP and SLA extracts was also assayed. We found that 22.2% (4/18) of the sera from healthy dogs vaccinated with Leishmune® showed optical densities (O.D.) values over the cut-off when the LRP extracts were used in the ELISA assays (FIG. 3B). When the same sera were analyzed in SLA based ELISA assays, a 16.6% (3/18) of the sera were also over the cut-off (FIG. 3B). None of the 23 sera obtained from dogs vaccinated with Leishtec® vaccine showed reactivity against SLA. Only one of these sera showed reactivity against LRP with an O.D. value close to the cut-off defied by the negative healthy control sera analyzed in the FIG. 2A.

Discussion

Many intracellular cytoplasmic or nuclear *Leishmania* proteins like histones, cysteine proteinases or kinesine, have been identified as antigenic in human or canine visceral *leishmaniasis* (VL) (2, 13, 14, 30, 32, 35). In this work we show that the parasite ribosomal proteins are also antigenic during CVL disease. Although some individual variability was observed between individual dogs, all the sera from symptomatic dogs showed reactivity against some of parasite ribosome constituents. Since the antigenicity of the parasite ribosomal proteins was also demonstrated in two different mice models of cutaneous *leishmaniasis* (22) our results indicate that the parasite ribosomes interact with the immune system of the vertebrate hosts during *Leishmania* natural and experimental infections.

Test based on serological techniques are the most frequent methods for diagnosis of canine and human visceral *leishmaniasis* (VL) due to the strong humoral response that accompanies the infection with viscerotropic *Leishmania* species. Taking into account the high reactivity observed against a parasite ribosome protein extract of the sera from dogs affected by CVL, we analyzed the diagnostic properties of the LRP extracts. Parasite ribosomal proteins were employed as the source of antigen in ELISA assays, since this technique is considered a precise and sensitive technique for the screening of large number of samples for the diagnosis of the VL disease (16, 33). A comparative analysis of the LRP extracts with total parasite proteins obtained from promastigote lysates was done because the use of crude SLA-based ELISA assays has usually shown to have high sensitivity for diagnosis of VL (5, 25, 33). The sensitivity and specificity values of the LRP extracts were similar to that showed by SLA when the sera of symptomatic and oligosymptomatics were analyzed. A slightly increase in sensitivity was obtained with LRP when compared with SLA (100% and 96%, respectively) and only one of the sera obtained from healthy dogs showed an absorbance value against LRP over the cut-off defined as the reactivity of the control sera. Thus, it can be concluded that the diagnostic performance of the LRP-based ELISA tests was similar to that obtained with the SLA preparation in the diagnosis of symptomatic or oligosymptomatic CVL. However, the detection of the disease in asymptomatic dogs may be critical in epidemiological studies for controlling the spread of the disease among dogs and also between dogs and humans (3, 20). Since SLA based ELISA failed to detect a great percentage of asymptomatic cases of CVL (27, 31) we analyzed the sensitivity of the LRP extracts in the diagnosis of asymptomatic CVL. Whereas the LRP antigen mixture detected all the asymptomatic cases (100%) the assay using SLA preparation only detected about 30% of the cases. Although the reactivity against LRP needs further confirmation using a larger number of oligosymptomatic and asymptomatic samples, our data indicate that LRP can be employed as a more sensitive antigen that SLA in the diagnosis of all forms of the CVL disease.

The specificity of the ELISA tests using SLA largely depends on the antigen preparation and some false positive results were obtained with the sera obtained from patients or dogs with co-endemic diseases such as Chagas' disease, *malaria*, leprosy or toxoplasmosis (16, 23, 31). For that reason several parasite recombinant proteins have been individually employed as antigen in ELISA assays for the development of more specific diagnostic test (24). Comparative ELISA assays generally revealed higher specificity but lower sensitivity when individual recombinant antigens where employed instead of SLA in the diagnosis of visceral human (25) or canine *leishmaniasis* diseases (31). Lower sensitivity values may be related with the variability observed in the heterogeneous humoral response elicited against parasite proteins in each patient or infected dog. Combination of non-related antigens (31) or production of poly-proteins containing several parasite antigens (6, 36) could further improve the performance of ELISA tests. Alternatively, purified parasite fractions containing different parasite antigens can be employed. Our results demonstrate that LRP extracts are not recognized by the sera from *T. cruzi* or *T. gondii* infected dogs whereas some of these sera showed a high reactivity against SLA.

The diagnosis specificity of the test should also be maintained when the sera are obtained from vaccinated dogs. Due to the existence of licensed commercial vaccines (15, 29) it would be desirable to differentiate infected dogs from vaccinated animals. Our results show that while some of the animals vaccinated with Leishmune® did show some reactivity against LRP and none of the animals vaccinated with Leishtec® did Taken together the results presented here demonstrate that the LRP extracts may be considered as an interesting alternative for use in ELISA diagnosis of CVL and mainly of asymptomatic animals for epidemiological studies in endemic areas.

TABLE 1

Sensitivity and specificity of ELISA assays using LRP and SLA for serodiagnosis of symptomatic CVL

|  | LRP | SLA |
|---|---|---|
| Sensitivity[a] | 100% (0/72) | 96% (3/72) |
| Specificity[b] | 98.2% (1/56) | 100% (0/56) |
| PVP[c] | 98.6% | 100% |
| PVN[d] | 100% | 94.9% |

[a]Sensitivity was calculated from the equation [(true positives/(true positives + false negatives) × 100]. The number of false negatives is indicated.
[b]Specificity was calculated from the equation [(true negatives/(true negatives + false positives) × 100]. The number of false positives is indicated.
[c]PVP. Predictive value of the positive was calculated from the equation [(true positives/(true positives + false positives) × 100].
[d]Sensitivity was calculated from the equation [(true negatives/(true negatives + true negatives) × 100].

REFERENCES

1. Alvar, J., C. Canavate, R. Molina, J. Moreno, and J. Nieto. 2004. Canine *leishmaniasis*. Adv Parasitol 57:1-88.
2. Badaro, R., D. Benson, M. C. Eulalio, M. Freire, S. Cunha, E. M. Netto, D. Pedral-Sampaio, C. Madureira, J. M. Burns, R. L. Houghton, J. R. David, and S. G. Reed. 1996. rK39: a cloned antigen of *Leishmania chagasi* that predicts active visceral *leishmaniasis*. J Infect Dis 173:758-61.
3. Baneth, G., A. F. Koutinas, L. Solano-Gallego, P. Bourdeau, and L. Ferrer. 2008. Canine *leishmaniosis*—new concepts and insights on an expanding zoonosis: part one. Trends Parasitol 24:324-30.
4. Barbiéri, C. L. 2006. Immunology of canine *leishmaniasis*. Parasite Immunol 28:329-37.
5. Barbosa-De-Deus, R., M. L. Dos Mares-Guia, A. Z. Nunes, K. M. Costa, R. G. Junqueira, W. Mayrink, O. Genaro, and C. A. Tavares. 2002. *Leishmania* major-like antigen for specific and sensitive serodiagnosis of human and canine visceral *leishmaniasis*. Clin Diagn Lab Immunol 9:1361-6.
6. Boarino, A., A. Scalone, L. Gradoni, E. Ferroglio, F. Vitale, R. Zanatta, M. G. Giuffrida, and S. Rosati. 2005. Development of recombinant chimeric antigen expressing immunodominant B epitopes of *Leishmania infantum* for serodiagnosis of visceral *leishmaniasis*. Clin Diagn Lab Immunol 12:647-53.
7. Bradford, M. M. 1976. A rapid and sensitive method for the quantitation of microgram quantities of protein utilizing the principle of protein-dye binding. Anal Biochem 72:248-54.
8. Cabrera, G. P., V. O. Da Silva, R. T. Da Costa, A. B. Reis, W. Mayrink, O. Genaro, and C. B. Palatnik-de-Sousa. 1999. The fucose-mannose ligand-ELISA in the diagnosis and prognosis of canine visceral *leishmaniasis* in Brazil. Am J Trop Med Hyg 61:296-301.
9. Cardoso, L., H. D. Schallig, F. Neto, N. Kroon, and M. Rodrigues. 2004. Serological survey of *Leishmania* infection in dogs from the municipality of Peso da Regua (Alto Douro, Portugal) using the direct agglutination test (DAT) and fast agglutination screening test (FAST). Acta Trop 91:95-100.
10. Carvalho, F. A., H. Charest, C. A. Tavares, G. Matlashewski, E. P. Valente, A. Rabello, R. T. Gazzinelli, and A. P. Fernandes. 2002. Diagnosis of American visceral *leishmaniasis* in humans and dogs using the recombinant *Leishmania donovani* A2 antigen. Diagn Microbiol Infect Dis 43:289-95.
11. Ciaramella, P., G. Oliva, R. D. Luna, L. Gradoni, R. Ambrosio, L. Cortese, A. Scalone, and A. Persechino. 1997. A retrospective clinical study of canine *leishmaniasis* in 150 dogs naturally infected by *Leishmania infantum*. Vet Rec 141:539-43.
12. Coelho, E. A., C. A. Tavares, F. A. Carvalho, K. F. Chaves, K. N. Teixeira, R. C. Rodrigues, H. Charest, G. Matlashewski, R. T. Gazzinelli, and A. P. Fernandes. 2003. Immune responses induced by the *Leishmania (Leishmania) donovani* A2 antigen, but not by the LACK antigen, are protective against experimental *Leishmania (Leishmania) amazonensis* infection. Infect Immun 71:3988-94.
13. Chang, K. P., and B. S. McGwire. 2002. Molecular determinants and regulation of *Leishmania* virulence. Kinetoplastid Biol Dis 1:1.
14. Chang, K. P., S. G. Reed, B. S. McGwire, and L. Soong. 2003. *Leishmania* model for microbial virulence: the relevance of parasite multiplication and pathoantigenicity. Acta Trop 85:375-90.
15. Fernandes, A. P., M. M. Costa, E. A. Coelho, M. S. Michalick, E. de Freitas, M. N. Melo, W. Luiz Tafuri, M. Resende Dde, V. Hermont, F. Abrantes Cde, and R. T. Gazzinelli. 2008. Protective immunity against challenge with *Leishmania (Leishmania) chagasi* in beagle dogs vaccinated with recombinant A2 protein. Vaccine 26:5888-95.
16. Ferreira Ede, C., M. de Lana, M. Carneiro, A. B. Reis, D. V. Paes, E. S. da Silva, H. Schallig, and C. M. Gontijo. 2007. Comparison of serological assays for the diagnosis of canine visceral *leishmaniasis* in animals presenting different clinical manifestations. Vet Parasitol 146:235-41.
17. Ferreira, W. A., W. Mayrink, M. L. dos Mares-Guia, and C. A. Tavares. 2003. Detection and characterization of *leishmania* antigens from an American cutaneous *leishmaniasis* vaccine for diagnosis of visceral *leishmaniasis*. Diagn Microbiol Infect Dis 45:35-43.
18. Garcia-Alonso, M., C. G. Nieto, A. Blanco, J. M. Requena, C. Alonso, and I. Navarrete. 1996. Presence of antibodies in the aqueous humour and cerebrospinal fluid during *Leishmania* infections in dogs. Pathological features at the central nervous system. Parasite Immunol 18:539-46.
19. Goto, Y., R. F. Howard, A. Bhatia, J. Trigo, M. Nakatani, E. M. Netto, and S. G. Reed. 2009. Distinct antigen recognition pattern during zoonotic visceral *leishmaniasis* in humans and dogs. Vet Parasitol 160:215-20.
20. Gramiccia, M., and L. Gradoni. 2005. The current status of zoonotic leishmaniases and approaches to disease control. Int J Parasitol 35:1169-80.
21. Herwaldt, B. L. 1999. Leishmaniasis. Lancet 354:1191-9.
22. Iborra, S., N. Parody, D. R. Abanades, P. Bonay, D. Prates, F. O. Novais, M. Barral-Netto, C. Alonso, and M. Soto. 2008. Vaccination with the *Leishmania* major ribosomal proteins plus CpG oligodeoxynucleotides induces protection against experimental cutaneous leishmaniasis in mice. Microbes Infect 10:1133-41.
23. Kar, K. 1995. Serodiagnosis of *leishmaniasis*. Crit Rev Microbiol 21:123-52.
24. Kubar, J., and K. Fragaki. 2005. Recombinant DNA-derived *leishmania* proteins: from the laboratory to the field. Lancet Infect Dis 5:107-14.
25. Maalej, I. A., M. Chenik, H. Louzir, A. Ben Salah, C. Bahloul, F. Amri, and K. Dellagi. 2003. Comparative evaluation of ELISAs based on ten recombinant or purified *Leishmania* antigens for the serodiagnosis of Mediterranean visceral leishmaniasis. Am J Trop Med Hyg 68:312-20.
26. Mauricio, I. L., J. R. Stothard, and M. A. Miles. 2000. The strange case of *Leishmania chagasi*. Parasitol Today 16:188-9.
27. Miro, G., L. Cardoso, M. G. Pennisi, G. Oliva, and G. Baneth. 2008. Canine *leishmaniosis*—new concepts and insights on an expanding zoonosis: part two. Trends Parasitol 24:371-7.
28. Nieto, C. G., I. Navarrete, M. A. Habela, F. Serrano, and E. Redondo. 1992. Pathological changes in kidneys of dogs with natural *Leishmania* infection. Vet Parasitol 45:33-47.
29. Palatnik-de-Sousa, C. B. 2008. Vaccines for *leishmaniasis* in the fore coming 25 years. Vaccine 26:1709-24.
30. Pollock, K. G., K. S. McNeil, J. C. Mottram, R. E. Lyons, J. M. Brewer, P. Scott, G. H. Coombs, and J. Alexander. 2003. The *Leishmania mexicana* cysteine protease, CPB2.8, induces potent Th2 responses. J Immunol 170: 1746-53.
31. Porrozzi, R., M. V. Santos da Costa, A. Teva, A. Falqueto, A. L. Ferreira, C. D. dos Santos, A. P. Fernandes, R. T. Gazzinelli, A. Campos-Neto, and G. Grimaldi, Jr. 2007. Comparative evaluation of enzyme-linked immunosorbent assays based on crude and recombinant leishmanial antigens for serodiagnosis of symptomatic and asymptomatic *Leishmania infantum* visceral infections in dogs. Clin Vaccine Immunol 14:544-8.
32. Rafati, S., A. Nakhaee, T. Taheri, A. Ghashghaii, A. H. Salmanian, M. Jimenez, M. Mohebali, S. Masina, and N. Fasel. 2003. Expression of cysteine proteinase type I and II of *Leishmania infantum* and their recognition by sera during canine and human visceral *leishmaniasis*. Exp Parasitol 103:143-51.
33. Reed, S. G., W. G. Shreffler, J. M. Burns, Jr., J. M. Scott, G. Orge Mda, H. W. Ghalib, M. Siddig, and R. Badaro. 1990. An improved serodiagnostic procedure for visceral *leishmaniasis*. Am J Trop Med Hyg 43:632-9.
34. Reis, A. B., A. Teixeira-Carvalho, A. M. Vale, M. J. Marques, R. C. Giunchetti, W. Mayrink, L. L. Guerra, R. A. Andrade, R. Correa-Oliveira, and O. A. Martins-Filho. 2006. Isotype patterns of immunoglobulins: hallmarks for clinical status and tissue parasite density in Brazilian dogs naturally infected by *Leishmania (Leishmania) chagasi*. Vet Immunol Immunopathol 112:102-16.
35. Requena, J. M., C. Alonso, and M. Soto. 2000. Evolutionarily conserved proteins as prominent immunogens during *Leishmania* infections. Parasitol Today 16:246-50.
36. Soto, M., J. M. Requena, L. Quijada, and C. Alonso. 1998. Multicomponent chimeric antigen for serodiagnosis of canine visceral *leishmaniasis*. J Clin Microbiol 36:58-63.

The invention claimed is:

1. A method for diagnosing Leishmaniasis in a subject comprising:
   (a) contacting a sample obtained from the subject with a Ribosomal Protein Extract (RPE) comprising at least two ribosomal proteins or fragments thereof, said RPE obtained by the following steps using a *Leishmania* cell that causes Leishmaniasis when present in a subject:
   (i) mixing said *Leishmania* cell with a lysis buffer to obtain a mixture, (ii) centrifuging the mixture of (i) to obtain a cytosolic extract,
(iii) treating/processing the cytosolic extract of (ii) to obtain said RPE;
(b) determining whether an immune response against an antigen derived from said RPE is present in the sample, and
(c) diagnosing the subject as having *Leishmania* if an immune response against an antigen derived from said RPE is present in the sample.

2. The method according to claim 1, wherein the ribosomal protein or fragment thereof is a fragment comprising at least 2, 3, 5, 7, 10, 15, 20, 25, 30 or more contiguous amino acids of said ribosomal protein.

3. The method according to claim 1, wherein the RPE does not comprise and does not consist of an epitope within amino acids 306-322 of SEQ ID NO: 1.

4. The method according to claim 1, wherein the parasitic disease is leishmaniasis and is caused by a *Leishmania* species.

5. The method according to claim 1, wherein the parasitic disease is caused by a different parasite species than the species from which the RPE was produced.

6. The method according to claim 3, wherein the RPE does not comprise and does not consist of an epitope in the amino acid sequence of SEQ ID NO:1.

7. The method according to claim 1 wherein the *Leishmania* species is *Leishmania* major.

8. The method of claim 1, wherein the diagnosis of Leishmaniasis is obtained on a presymptomatic or asymptomatic subject.

9. The method of claim 1, wherein the subject is a dog or human being.

10. The method of claim 1, wherein the method further comprises determining whether an antibody recognizing a *Leishmania* antigen not derived from an RPE is present in said sample from said subject.

11. The method of claim 10, wherein said another *Leishmania* antigen is selected from a polyprotein containing several *Leishmania* proteins and a *Leishmania* histone protein.

12. The method of claim 1, wherein step (b) comprises determining whether an antibody recognizing an antigen derived from said RPE is present in the sample and wherein the subject is diagnosed as having *Leishmania* according to step (c) if an antibody recognizing an antigen derived from said RPE is present in the sample.

13. An assay for diagnosing Leishmaniasis in a subject, comprising identifying the presence of an antibody in the subject that binds to a *Leishmania*-derived RPE.

14. An assay according to claim 13, that is an enzyme-linked immunosorbent assay (ELISA).

* * * * *